(12) United States Patent
Breuer et al.

(10) Patent No.: US 10,082,484 B2
(45) Date of Patent: Sep. 25, 2018

(54) GAS-SENSITIVE HALL DEVICE

(71) Applicant: Infineon Technologies AG, Neubiberg (DE)

(72) Inventors: Werner Breuer, Sinzing-Viehhausen (DE); Markus Eckinger, Regenstauf (DE)

(73) Assignee: Infineon Technologies AG, Neubiberg (DE)

( * ) Notice: Subject to any disclaimer, the term of this patent is extended or adjusted under 35 U.S.C. 154(b) by 0 days.

(21) Appl. No.: 15/247,336

(22) Filed: Aug. 25, 2016

(65) Prior Publication Data

US 2017/0082581 A1    Mar. 23, 2017

(30) Foreign Application Priority Data

Sep. 17, 2015 (DE) .......................... 10 2015 115 667

(51) Int. Cl.
*G01N 27/74* (2006.01)
*G01R 33/07* (2006.01)
*G01N 27/72* (2006.01)

(52) U.S. Cl.
CPC ............. *G01N 27/74* (2013.01); *G01N 27/72* (2013.01); *G01R 33/072* (2013.01)

(58) Field of Classification Search
None
See application file for complete search history.

(56) References Cited

U.S. PATENT DOCUMENTS

| 8,957,687 | B2* | 2/2015 | Nackaerts | G01N 27/414 324/438 |
| 2002/0186584 | A1* | 12/2002 | McDowell | G11C 11/16 365/171 |
| 2007/0045756 | A1* | 3/2007 | Chang | B82Y 10/00 257/414 |
| 2011/0199102 | A1 | 8/2011 | Garcia et al. | |

(Continued)

FOREIGN PATENT DOCUMENTS

| CN | 103123953 A | 5/2013 |
| CN | 104049002 A | 9/2014 |
| CN | 104535623 A | 4/2015 |

OTHER PUBLICATIONS

Office Action dated Aug. 29, 2016 for German Patent Application No. 102015115667.9.

(Continued)

*Primary Examiner* — Jermele M Hollington
*Assistant Examiner* — Douglas X Rodriguez
(74) *Attorney, Agent, or Firm* — Schiff Hardin LLP

(57) ABSTRACT

A chemically sensitive Hall device is described herein. In accordance with one example of the present invention, a Hall device comprises a substrate and a chemically sensitive layer arranged on the substrate. The chemically sensitive layer is able to interact with atoms or molecules of a gaseous or liquid fluid. Force electrodes are connected to the chemically sensitive layer for feeding a sensor current through the chemically sensitive layer along a first direction. Sense electrodes are connected to the chemically sensitive layer to tap a Hall voltage at the chemically sensitive layer along a second direction. A back gate is arranged on or integrated in the substrate and is isolated from the chemically sensitive layer by an isolation layer.

27 Claims, 9 Drawing Sheets

(56) References Cited

U.S. PATENT DOCUMENTS

2013/0018599 A1* 1/2013 Peng .................. B82Y 15/00
  702/30
2014/0128278 A1  5/2014 Fahmy et al.

OTHER PUBLICATIONS

Office Action dated May 3, 2018 for Chinese Patent Application No. 201610819317.7.

* cited by examiner

GAS-SENSITIVE HALL DEVICE

TECHNICAL FIELD

The invention relates to the field of gas sensors. In particular to a gas-sensitive Hall device for detecting specific gases using the Hal effect.

BACKGROUND

Gas sensors can be used to measure the concentration of a target gas. In most gas sensors the target gas is oxidized or reduced an electrode which results in a measureable sensor current. Integrated gas sensors utilize gas sensitive layers disposed on a semiconductor substrate. Many commercial chemical gas sensors utilize gas-sensitive metal oxide (MOX) layers disposed on semiconductor material. Such sensors may be produced at comparably low costs and exhibit a high sensitivity. Among MOX materials tin oxide is frequently used in solid-state sensors.

Recently graphene is used as a gas-sensitive sensor material due to its unique electrical properties. The band structure of graphene makes it particularly sensitive to chemical doping. The withdrawal or donation of even a few electrons shifts the Fermi level significantly away from the Dirac point, and thus even a small change in the number of charge carriers has a significant effect on the resistance of a graphene layer. Apart from its band structure, graphene has many other properties that render it particularly suitable for applications in gas sensors. Single-layer graphene has every atom at the surface, has a high metallic conductivity, even when very few charge carriers are present. Furthermore, it has and few crystal defects, which leads to low Johnson noise. The low noise level in graphene devices means that very small changes in resistivity (i.e. small sensor responses) can be measured, leading to highly sensitive sensors. Graphene is also chemically very stable due to its strong bonds and lack of defects. The electric conductivity of graphene allows for direct measurement of resistance, and the robustness of graphene allows for layers, which only one atom thick, to be processed into gas sensors.

Other gas sensors utilize a layer of two-dimensional electron gas (2DEG), which are sensitive to the presence of specific gases. For example, the two-dimensional electron gas (2DEG) formed at the interface of AlGaN/GaN layers grown on silicon substrates may be used for the detection of nitrogen oxides ($NO_x$). In the presence of humidity, the interaction of nitrogen oxide with an open gate area may reversibly changes the conductivity of the 2DEG.

As outlined above, the measureable effect in solid-state gas sensors is usually a change of the electric conductivity (or resistivity) of gas-sensitive layers. Recent research has shown that gas sensitive layers (or generally chemically sensitive layers) such as graphene layers may also be used to form Hall bars. The measureable transversal voltage (e.g. the Hall voltage) due to the Hall effect shows also significant sensitivity to the presence of specific atoms or molecules of gaseous or liquid fluids. It is thus an object of the present invention to provide a sensor which makes use of the Hall effect in chemically sensitive layers.

SUMMARY

The above-mentioned object is achieved by the chemically sensitive Hall device in accordance with claim 1, by the sensor arrays of claims 19 and 25 or by the method of claim 13. Various embodiments and further developments are covered by the dependent claims.

A chemically sensitive Hall device is described herein. In accordance with one example of the present invention, a Hall device comprises a substrate and a chemically sensitive layer arranged on the substrate. The chemically sensitive layer is able to interact with atoms or molecules of a gaseous or liquid fluid. Force electrodes are connected to the chemically sensitive layer for feeding a sensor current through the chemically sensitive layer along a first direction. Sense electrodes are connected to the chemically sensitive layer to tap a Hall voltage at the chemically sensitive layer along a second direction. A back gate is arranged on or integrated in the substrate and is isolated from the chemically sensitive layer by an isolation layer.

Furthermore, a chemically sensitive sensor array is described. In accordance with one example of the invention, the sensor array comprises at least two Hall elements having a chemically sensitive layer, which is able to interact with atoms or molecules of a gaseous or liquid fluid. Each Hall element having force electrodes for feeding a sensor current through the respective Hall element, sense electrodes for tapping a Hall voltage at the respective Hall element, and a back gate, which is arranged subjacent to the chemically sensitive layer and isolated from the chemically sensitive layer by an isolation layer.

Moreover, a method for operating a sensor including a chemically sensitive Hall element is described. In accordance with one example of the invention a sensor current is applied to the chemically sensitive Hall element, which is arranged on a substrate, so that the sensor current passes through the Hall element in a first direction. A Hall voltage is sensed at the Hall element along a second direction, which is substantially perpendicular to the first direction. A gate voltage, which is responsive to the Hall voltage, is applied to a back-gate, wherein the back-gate arranged on or integrated in the substrate.

BRIEF DESCRIPTION OF THE DRAWINGS

The invention can be better understood with reference to the following description and drawings. The components in the figures are not necessarily to scale, emphasis instead being placed upon illustrating the principles of the invention. Moreover, in the figures, like reference numerals designate corresponding parts. In the drawings.

DETAILED DESCRIPTION

In the exemplary embodiments described below, a graphene layer is used as one possible option for a gas-sensitive layer. However, other materials may be used as an alternative to graphene. The choice of the material may depend on the actual application and particularly on the physical and chemical properties of the gas molecules to be detected.

Figure 1:
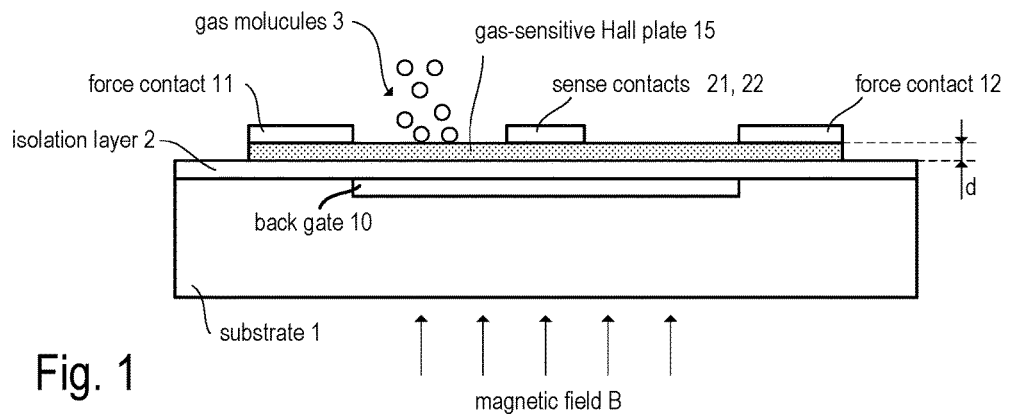
FIG. 1 is a cross-sectional view of a first exemplary embodiment of a gas-sensitive Hall element including a back gate to control the charge carrier density in the gas sensitive layer of the Hall element.
Figure 2:
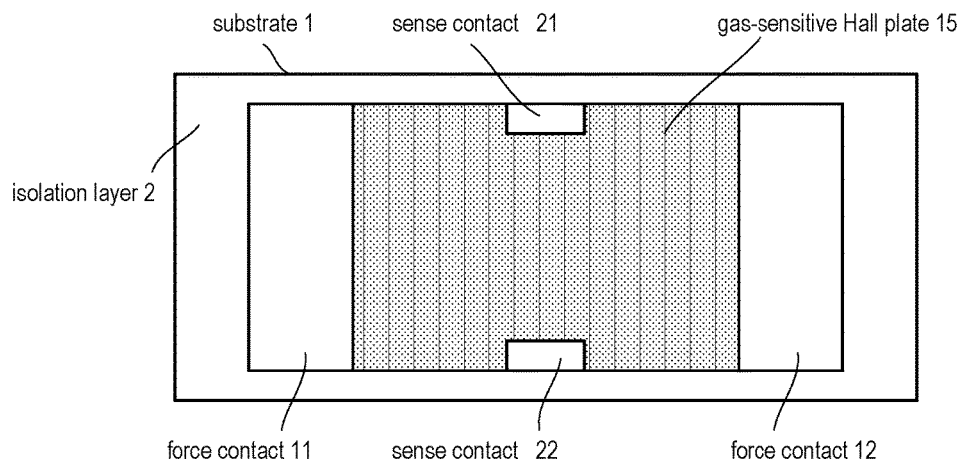
FIG. 2 is a top view corresponding to the cross-sectional view of FIG. 1

FIG. 1 is a cross-sectional view of an exemplary solid-state gas sensor formed on a silicon substrate 1. FIG. 2 illustrates the corresponding top view. It is noted that other substrate materials may be used as an alternative to silicon. The present illustration shows only the structure of a gas sensor. However, other components and circuits (e.g. control, driver and evaluation circuits) may be integrated in the same substrate and/or in the same chip package as the gas sensor.

A conductive back-gate region 10 is formed in the substrate 1, for example by deposition of a metal layer (e.g. in a recess on the top surface of the substrate) or by generating a doped semiconductor region, e.g. by diffusion of dopants, ion implantation or the like. Alternatively, a layer of ply-cristalline silicon (polysilicon) may be deposited to form the back gate region 10. An isolation layer 2 is formed on the top surface of the substrate 1 so that the isolation layer 2 covers the back-gate region 10 from a gas sensitive layer 15 that is formed on top of the isolation layer 2. In case graphene is used as gas sensitive material for forming the gas-sensitive layer 15, the isolation layer 2 may be made of hexagonal boron nitride (h-BN). Boron nitride is isoelectronic to graphene, and a h-BN underlayment may reduce corrugation of the graphene layer (as compared with using a silicon oxide isolation layer) as well as spatial inhomogeneity of charge carrier density in the graphene layer 15. As mentioned above, the Hall effect, which occurs in the gas-sensitive layer 15 when exposed to a magnetic field B, is to be evaluated in order to detect gas molecules or measure gas concentration. Therefore, the gas-sensitive layer 15 can be regarded as Hall plate (sometimes also referred to as Hall bar). Alternatively, the isolation layer 2 may be formed using Molybdenum disulfide ($MoS_2$) or an oxide or a nitride of other materials (e.g. silicon oxide). As mentioned above, layers forming a two-dimensional electron gases (2DEG) may be used instead of graphene to form the gas-sensitive layer 15. 2DEG layers may occur in III-V semiconductor heterostructures based on, e.g., InAs, InSb, GaAs, GaN, etc. The purpose and the function of the back gate is describes later with reference to Figures 8 and 9.

The gas-sensitive Hall plate 15 is contacted by the force contact electrodes 11 and 12, as well as by the sense contact electrodes 21 and 22 (see also top view of FIG. 2), which contact the top surface of the Hall plate 15. The force contact electrodes 11, 12 may be formed by a metal (e.g. gold, aluminum, etc.) and are arranged at opposing ends of the gas-sensitive Hall plate 15 along a longitudinal direction. The sense contact electrodes 21, 22 may also be formed by a metal (e.g. gold, aluminum, etc.) but are arranged at opposing ends of the gas-sensitive Hall plate 15 along a transverse direction (which is perpendicular to the longitudinal direction). The sense contact electrodes 11, 12 are used to feed a sensor current $i_H$ through the gas-sensitive Hall plate 15 so that the sensor current $i_H$ passes through the Hall plate 15 substantially along the longitudinal direction. Due to the Hall effect a voltage arises transversely across the current-carrying Hall plate 15 when being exposed to the magnetic field B, which is oriented perpendicularly to the top surface of the Hall plate 15. This voltage is also referred to as "Hall voltage" and can be tapped at the Hall plate 15 via the sense contact electrodes 21, 22.

Figure 3:
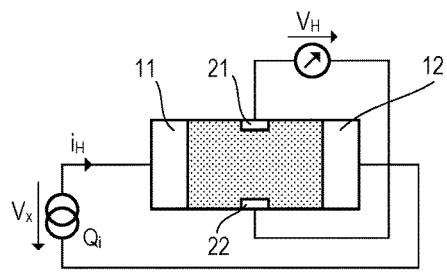
FIG. 3 is a circuit diagram illustrating the use of the Hall element of FIGS. 1 and 2.

FIG. 3 illustrates the above-explained situation with the help of a circuit diagram. Accordingly, a current source $Q_i$ generates the sensor current $i_H$ that is applied to the first force contact electrode 11, and drained from the second force contact electrode 12. When exposed to a magnetic field as illustrated in FIG. 1, the Hall voltage $V_H$ arises between the sense contacts 21 and 22. In FIG. 3 a meter is connected to the sense contacts 21 and 22. It is, however, understood, that this meter is merely representative for any circuit that is used to process the Hall voltage $V_H$ in order to determine the desired output indicative of gas molecules 3 interacting with the gas-sensitive Hall plate 15 (see FIG. 1).

The Hall voltage $V_H$ can be calculated in accordance with the following equation $$V_H = R_H \cdot i_H \cdot B / d, \quad (1)$$

wherein d is the thickness of the gas-sensitive Hall plate (see FIG. 1). The proportionality factor $R_H$ is generally referred to as Hall constant and has the dimension cubic meter per Coulomb. It can be calculated as:

$$RH = (n \cdot q)^{-1}. \quad (2)$$

In equation 2, the parameter n denotes the charge carrier density (e.g. electrons per cubic meter) and the parameter q denotes the charge per charge carrier (e.g. the elementary charge $-1,602 \cdot 10^{-19}$ C in case of electrons). In case of electron conduction (q=−e) the Hall constant can also be expressed as:

$$R_H = \rho \cdot \mu = \mu / \sigma, \quad (3)$$

wherein ρ denotes the specific resistance of the Hall plate 15 (σ the respective conductivity), and μ denotes the electron mobility. In view of equations 2 and 3 the Hall constant basically depends on the conductivity (which is proportional to the charge carrier density) as well as on the charge carrier mobility.

Gas molecules 3 (see FIG. 1) may be detected as the molecules are adsorbed at the surface of the gas-sensitive layer 15. Due to this interaction between the gas-sensitive layer 15 and the gas molecules 3, the charge-carrier density or the charge carrier mobility (or both) of the layer 15 changes, which results in a respective change of the Hall constant $R_H$ and also the specific resistance p of the gas-sensitive layer 15. In gas-sensitive resistive sensors the mentioned change of the specific resistance is measured using Ohm's law thereby producing a comparably small sensor signal. In contrast thereto, the effect is significantly larger when evaluating the Hall voltage. The lower the charge carrier density and the higher the charge carrier mobility, the higher is the Hall constant. The Hall effect can further be "amplified" by the factor B/d (see FIG. 1), when the gas sensitive layer 15 (Hall plate) is thin (d is small) and the magnetic flux density B is high. Thus, highly sensitive gas sensors can be constructed by using thin gas-sensitive layers has Hall plates.

Figure 4:
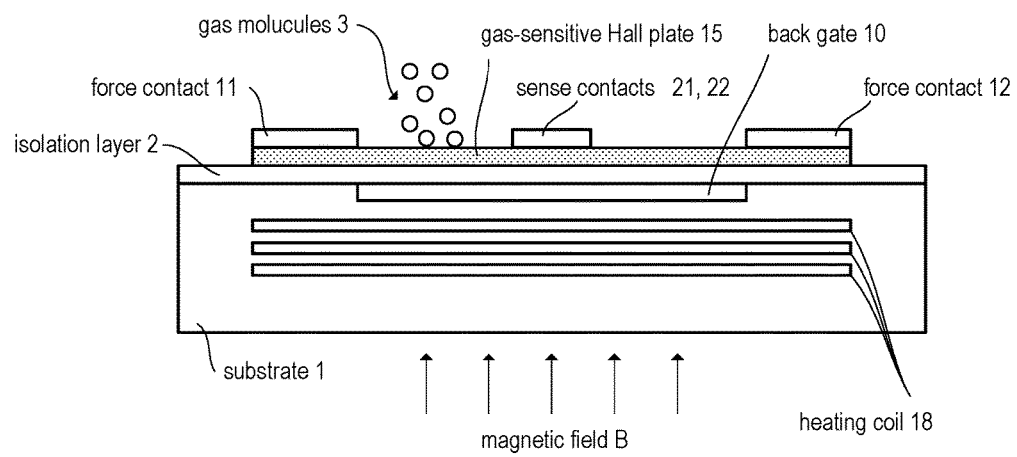
FIG. 4 is a cross-sectional view of a second exemplary embodiment of a gas-sensitive Hall element including a heating coil to regenerate the gas-sensitive layer of the Hall element.

FIG. 4 illustrates a cross-sectional view of another exemplary embodiment of a gas-sensitive Hall sensor. The example of FIG. 4 is essentially identical with the previous example of FIG. 1 except that an additional coil 18 is provided in the substrate 1. The coil may be integrated in the silicon substrates using any known techniques. Similar techniques are used to produce coils for integrated coreless transformers or the like. The coil 18 may be used to generate the magnetic field B (during a measurement period) and/or to generate heat to heat up the gas-sensitive layer for desorbing gas molecules from the gas-sensitive layer 15 (during a regeneration period). For the purpose of heating, a polysilicon (polycrystalline silicon) micro-heater may be used instead of the coil 18 (see description with reference to FIG. 6). Apart from the coil 18, the components shown in FIG. 4 are identical with FIG. 1 and the respective explanation is therefore not repeated here.

Figure 5:
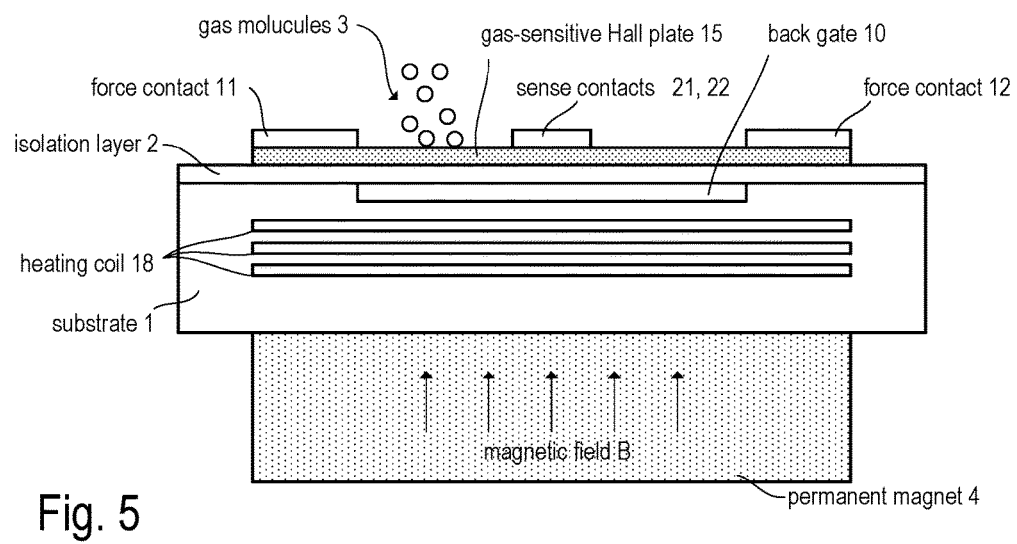
FIG. 5 is a cross-sectional view of a third exemplary embodiment of a gas-sensitive Hall element including a permanent magnet to generate a magnetic field to magnetically bias the Hall element.

FIG. 5 illustrates a cross-sectional view of another exemplary embodiment of a gas-sensitive Hall sensor. The example of FIG. 5 is essentially identical with the previous FIG. 4 but with an additional permanent magnet 4 arranged subjacent to the semiconductor substrate 1. The permanent magnet 4 is vertically magnetized to generate a vertically oriented (i.e. perpendicular to the surface of the Hall plate 15) magnetic field B, which is needed for the operation of the gas sensor. In this case the heating coil 18 is used for the heating (regeneration) of the gas-sensitive layer 15. Apart from the permanent magnet 4, the components shown in FIG. 5 are identical with FIG. 4 and the respective explanation is therefore not repeated here.

Figure 6:
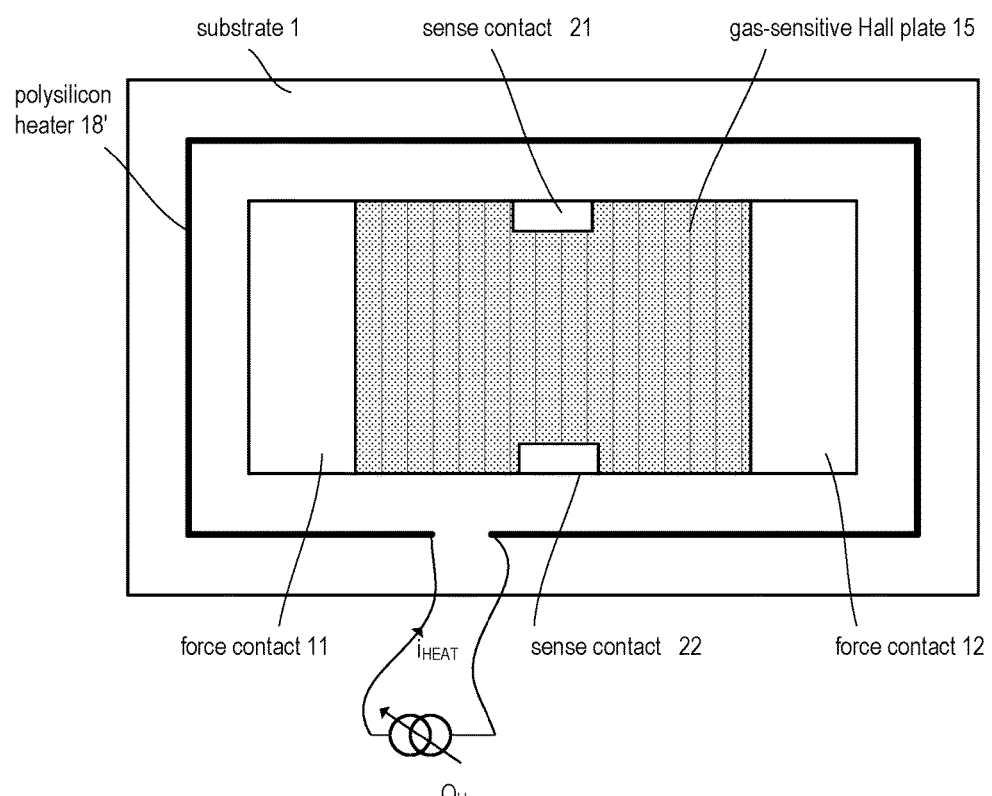
FIG. 6 illustrates a top view of a further exemplary embodiment of a gas-sensitive Hall element including a micro-heater (polycrystalline silicon resistor used for heating)

FIG. 6 is a top view illustrating essentially the same example as shown in FIG. 2 but with an additional polysilicon micro-heater arranged on the substrate 1 around the gas sensitive Hall plate 15. The micro-heater is formed by a strip line made of polysilicon. However, materials other than polysilicon (e.g. metals) may be used instead. The strip line forms a loop on the substrate 1 around the Hall plate 15. However, the strip lines may also be provided below the Hall plate 15 (below the isolation layer 2, see FIG. 1) and may also have a different geometry (e.g. a meander shape). When supplied with a current $i_{HEAT}$ the energy $R_{POLY}^2 \cdot i_{HEAT}$ is dissipated into the substrate and the local temperature of the substrate 1 and thus the temperature of the Hall plate 15 increases. The controllable current source $Q_H$ is representative for any electronic circuit that is configured to provide the current $i_{HEAT}$ for the micro-heater. As mentioned the micro-heater may be activated periodically to "refresh" the Hall plate 15 (desorb the gas atoms/molecules from the Hall plate) in each measurement cycle. In case the back-gate region 10 (not shown in the top view, see cross section of FIG. 1) is formed by a polysilicon layer, the back-gate region may additionally be used as a micro-heater, thus avoiding the need for a separate micro-heater.

Figure 7A:
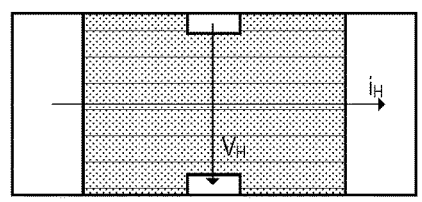
FIGS. 7A-7E illustrates top views of different geometries, which may be used to form a Hall element.
Figure 7B:
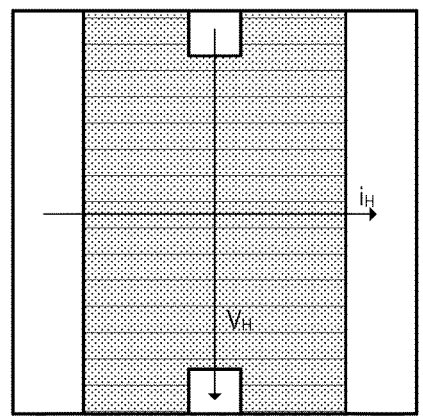
Figure 7C:
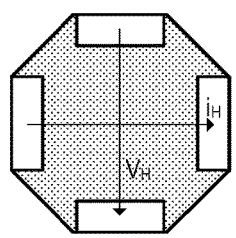
Figure 7D:
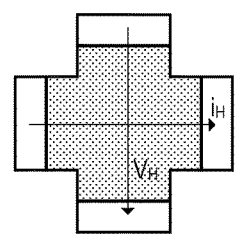
Figure 7E:
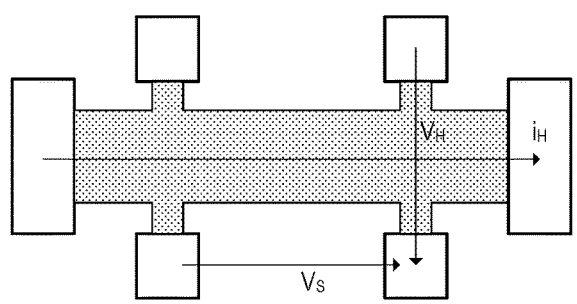

In the examples of FIGS. 1 to 6 the Hall plate 15 has a the shape of a rectangular plate. However, the Hall plate 15 does not necessarily have to have a rectangular layout. FIG. 7 (7A-7D) illustrates top views of different possible layouts for the Hall plate 15. FIG. 7A shows a rectangular shape as in the previous examples. FIG. 7B illustrates a quadratic layout, FIG. 7C an octagonal layout, and FIG. 7D shows a complex polygon layout in the shape of a cross. Various further layouts are possible. The exemplary layout in FIG. 7E allows the measurement of the Hall voltage $V_H$ (in a transversal direction) as well as the voltage drop $V_S$ due to the ohmic resistance $R_{XX}$ of the Hall plate 15 (see also FIG. 8, top diagram), wherein $V_S = R_{XX} \cdot i_H$.

Figure 8:
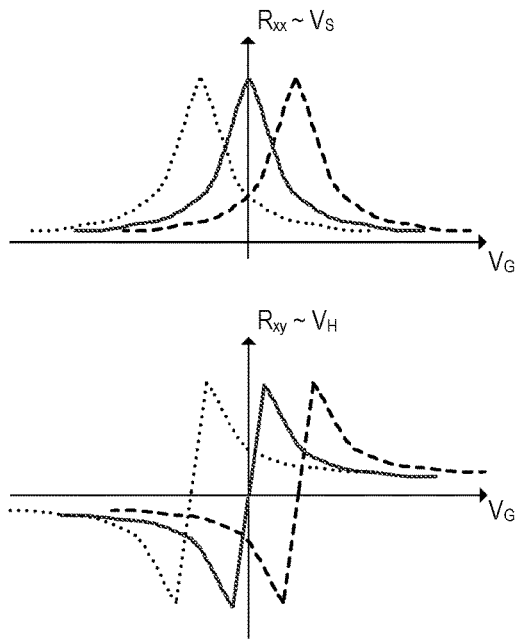
FIG. 8 includes two diagrams illustrating the ohmic resistivity and the Hall resistivity with regard to the gate voltage applied to the back gate a the gas sensor in accordance with FIG. 1.

As mentioned above the charge carrier density n in the gas-sensitive layer 15 (see examples of FIGS. 1 to 5) affects the Hall constant $R_H$ (see equation 2), and the charge carrier density n is affected by gas molecules 3 adsorbed at the surface of the gas-sensitive layer 15 (Hall plate). Generally, the Hall constant $R_H$ increases as the charge carrier density n decreases. The charge carrier density n may also be controlled by applying a gate voltage $V_G$ to the back-gate region 10 (see FIGS. 1, 4, and 5). The diagrams of FIG. 87 illustrate how the voltage $V_G$ affects the (ohmic) resistance $R_{XX}$ of the gas-sensitive layer 15 (see top diagram of FIG. 8) and the Hall constant RH (see bottom diagram of FIG. 8). The solid lines in the diagrams of FIG. 8 represent a situation, in which no gas molecules 3 are present, which could be adsorbed at the gas-sensitive layer 15. The characteristic curves (solid lines) are shifted to the right or the left in the presence of gas molecules 3. In case the gas molecules are donators (e.g. $NH_3$) the curve is shifted to the right (dotted line), in case the gas molecules are acceptors ($NO_2$) the curve is shifted to the right (dashed line). In other words, the gate voltage $V_G$ may be varied to "calibrate" the Hall plate. Furthermore, the back-gate allows to "switch" between electron conduction and hole conduction by applying an appropriate gate voltage $V_G$, wherein the Hall constant $R_H$ is positive for hole conduction and negative in case of electron conduction. When holes and electrons are balanced (at the socalled Dirac point), then the Hall constant is zero.

Figure 9:
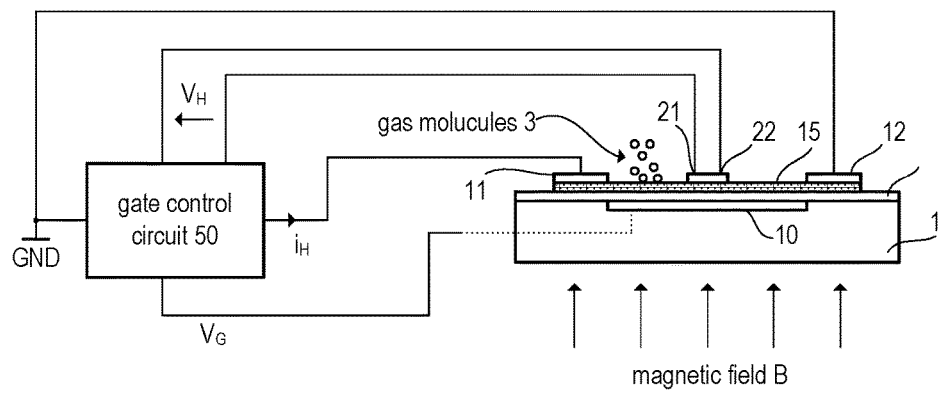
FIG. 9 illustrates one exemplary circuit for controlling the gate voltage applied to the back gate of a gas sensor in accordance with FIG. 1.

FIG. 9 is a circuit diagram illustrating one exemplary circuit arrangement, which may be used to drive the gas sensor and to control the gate voltage $V_G$ applied to the back gate 10 of the gas sensor. In the present example, the a sensor control unit 50, which includes a gate control circuit, provides a constant sensor current $i_H$ which is fed through the gas-sensitive Hall plate 15 (see FIG. 1) via the force contacts 11 and 12. Before starting actual measurements, the resulting Hall voltage $V_H$ (see equation 1) may be regulated to zero by appropriately tuning the gate voltage $V_G$ applied to the back gate 10 of the gas sensor (see also FIG. 1). Such a calibration $V_H=0$) allows a highly sensitive detection/measurement of gas molecules or changes of the gas molecule concentration in the ambient atmosphere. Moreover, it allows to distinguish between gas molecules, which act as donators (e.g. $NH_3$) or acceptors (e.g., $NO_2$). Therefore, the sensor can also be used in liquids to distinguish $OH^-$ (hydroxide) and $H_3O^+$ (oxonium) ions, i.e. for the measurement of pH value. In this context it should be noted that, dependent on the material used for the Hall plate 12, the embodiments described herein may also be used within a liquid atmosphere instead of a gaseous atmosphere. The term "chemically sensitive" is used as a collective term for both, "gas-sensitive" and "sensitive to liquids".

In one exemplary embodiment, the Hall voltage $V_H$ is continuously regulated to zero (for a constant magnetic field B). In this case the gas sensor is continuously operated in the Dirac point, and the gate voltage $V_G$, which is necessary to make the Hall voltage $V_H$ zero, may be used as sensor signal which is indicative for the presence of gas molecules.

Figure 10:
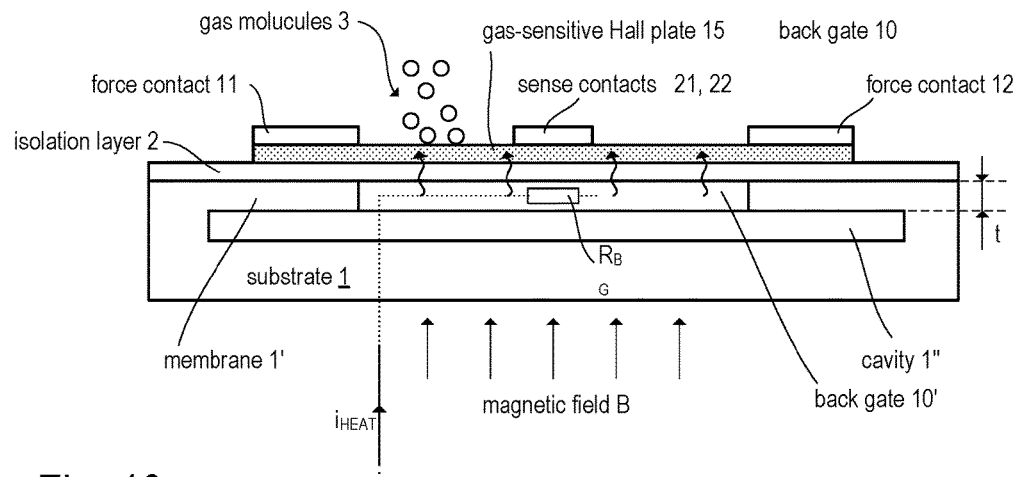
FIG. 10 is a cross-sectional view of a first exemplary embodiment of a gas-sensitive Hall element, which is formed on a silicon membrane.

As mentioned above with reference to FIG. 4, a microheater may be provided to heat up the gas-sensitive Hall plate 15 in order to resorb the gas molecules previously adsorbed at the surface of the gas-sensitive Hall plate 15. While in the previous example of FIG. 4 a heating coil is used to heat up the substrate and thus the Hall plate 15, an electrical current /HEAT is fed through the back-gate region 10 instead. The electrical resistance of the back-gate region 10 (symbolized in FIG. 10 by the resistor $R_{BG}$) causes a dissipated power of $i_{HEAT}^2 \cdot R_{BG}$, which heats up the back-gate region 10 and thus also the superjacent gas-sensitive Hall plate 15. In order to achieve the desired increase in temperature, the heat capacity of the heated material should be small. This is the case when the mass of the heated material is small; and this can be achieved by forming the gas-sensitive layer 15 on a membrane 1' as shown in the example of FIG. 10. The cavity 1" in the substrate 1 below the membrane 1' is an effective heat insulation and thus most of the heat generated by the current $i_{HEAT}$ in the back gate region 10 is dissipated through the Hall plate 15.

For repeated measurements, the gas-sensitive layer 15 may cyclically be regenerated by heating (see FIGS. 4, 5, and 10). After regeneration of the gas-sensitive layer 15, a calibration (i.e. tuning of the gate voltage $V_G$) may subsequently be performed as explained with reference to FIG. 9.

Figure 11:
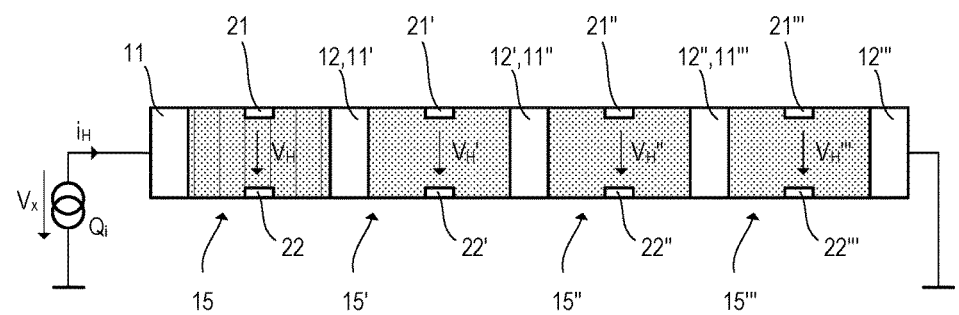
FIG. 11 is a top view of an array of a Hall elements which may be used for differential measurements or detection of different gases.

FIG. 11 illustrates an array of Hall plates 15, 15', 15", 15''', which are connected in series such that they carry the same sensor current $i_H$ provided by the current source $Q_i$ (see FIG. 3). In the present case the array is composed of four Hall plates 15. However, in different embodiments only two Hall plates may be provided (e.g. for differential measurements). Other embodiments may include three or more Hall plates. Due to the series connection the force contact 12 of the first Hall plate 15 and the force contact 11' of the second Hall plate 15' may formed as one piece. The sensitivity to gas atoms or molecules may be different for the different Hall plates 15, 15', 15" and 15'''. In this case the Hall voltages $V_H$, $V_H'$, $V_H''$ and $V_H'''$, which may be tapped at the Hall plates 15, 15', 15" and 15''', respectively, are different and may be indicative for the gas or specific gas components interacting with the Hall plates. The array of Hall plates 15, 15', 15" and 15''' may be formed on one single semiconductor chip. Alternatively, separate chips may be used for the different hall plates, which may be, however, included in the same chip package. In case of differential measurements an array of two Hall plates 15 and 15' may be used, wherein on Hall plate is passivated so that it cannot interact with gas molecules in the environment. Both Hall plates 15 and 15' "see" the same sensor current $i_H$ and the same magnetic field B, but only one Hall plate is subjected to the gas. In this case the difference $V_H-V_H'$ of the Hall voltages $V_H$ and $V_H'$ of the two hall plates may be evaluated to detect the gas atoms/molecules and/or to measure their concentration in the surrounding atmosphere.

Figure 12:
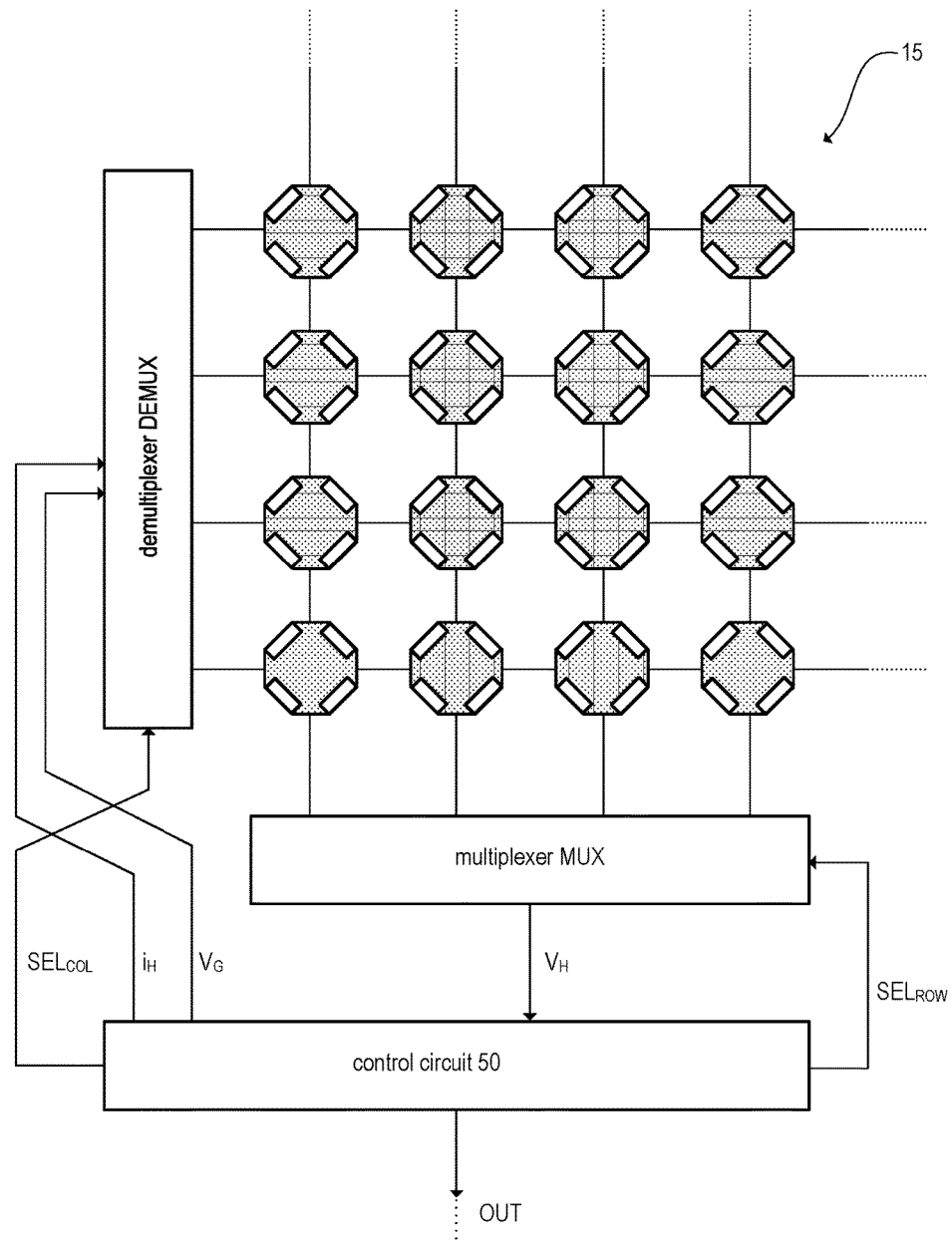
FIG. 12 schematically illustrates another example of an array of Hall elements which may be controlled using multiplexer/demultiplexer circuits to select one or more specific Hall elements of the array.

FIG. 12 schematically illustrates another example of an array of Hall elements which may be controlled using multiplexer/demultiplexer circuits to select one or more specific Hall elements of the array. By appropriate control of the multiplexer MUX and demultiplexer DEMUX one or more individual Hall plates 15 of the array may be chosen and used for a specific measurement. The Hall plates 15 may be arranged matrix-like and distributed along rows and columns as shown in FIG. 12. However, alternative arrangements are possible. The control unit 50 may perform a similar function as the control circuit 50 shown in FIG. 9. That is, the control unit 50 provides a sensor current $i_H$ to a selected Hall element 15, receives the Hall voltage $V_H$ tapped at the selected Hall element 15, and applies a gate voltage $V_G$ to the selected Hall element 15. Dependent on the actual implementation, the gate voltage $V_G$ may be regulated such that the Hall Voltage $V_H$ remains at a setpoint of zero volts. However, different regulation schemes may be used. A Hall element may be selected by the select signals $SEL_{ROW}$ and $SEL_{COL}$ supplied to the multiplexer MUX and the demultiplexer DEMUX, respectively. The multiplexer MUX is configured to direct a signal (e.g. the gate voltage $V_G$ and/or the sensor current $i_H$ or signals representing $V_G$ or $i_H$, a signal for activating the microheater, etc.) to a Hall element identified by the select signal $S_{ROW}$. The demultiplexer DEMUX is configured to direct a signal (e.g. the Hall voltage $V_H$ or a signal representing $V_H$) tapped at a Hall element identified by the select signal $S_{COL}$ to the control circuit 50.

In the present example as described above, a specific Hall element may be selected and then used for the detection of gas atoms/molecules and/or for measurement of concentration of gas atoms/molecules in the surrounding atmosphere. Each Hall element may be differently chemically functionalized to be sensitive for different gas atoms/molecules. By making a sequence of measurements and sequentially selecting different Hall elements, different types of gases may be identified. Moreover, more than one Hall elements may be selected at one time. In that case, two or more Hall elements may be connected in parallel to increase sensitivity (as the total chemically active area of the gas sensitive layers 15 increases). In this context "connected in parallel" means that the sensor outputs (where the Hall voltage $V_H$ is tapped) are connected in parallel. With regard to the sensor current $i_H$ the Hall elements 15 are connected in series so that every Hall element 15 carries the same sensor current $i_H$.

Figure 13:
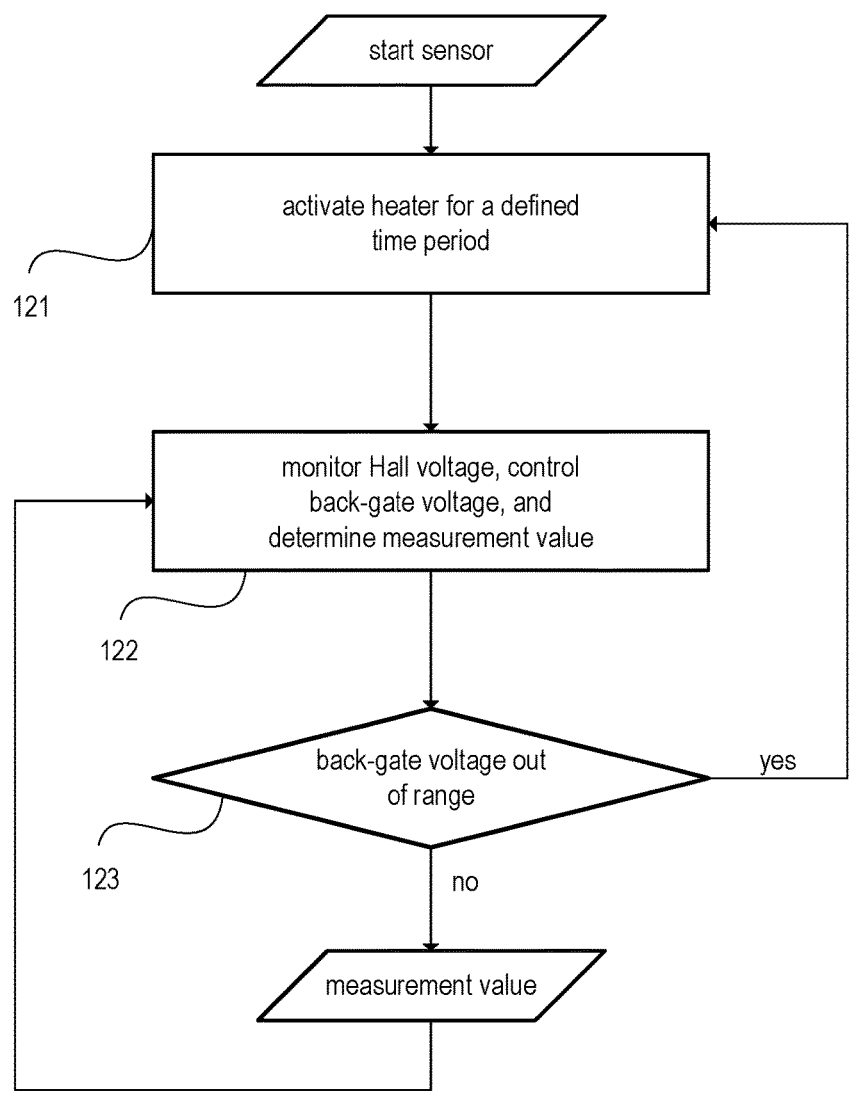
FIG. 13 illustrates a flow chart illustrating a method of operating the gas sensors described herein.

FIG. 13 illustrates a flow chart illustrating a method of operating the gas sensors described herein. The method may be implemented, for example, by using an appropriately configured control unit such as the sensor control unit 50 in the example of FIG. 9. At the beginning of measurements, the gas sensitive hall plate is "refreshed" by heating up the sensor. The heating results in a desorption of gas molecules/atoms that have previously been adsorbed at the surface of the gas-sensitive Hall plate (see FIG. 5). For this purpose the micro-heater included in the sensor may be activated for a defined time period (and deactivated after that time period, see FIG. 13, step 121). During operation of the sensor, the Hall voltage is continuously monitored (see FIG. 9) and the gate voltage $V_G$, which is applied to the back gate region 10 of the sensor (see, e.g., FIG. 5), is controlled such that the sensor is operated in a defined operating point (cf. the explanations with reference to FIGS. 8 and 9). The Hall voltage can be processed (e.g. digitized) to obtain a measurement value in the desired form (see FIG. 13, step 122). However, the desired information is already in the Hall voltage $V_H$ and/or the back-gate voltage $V_G$. Due to the adjustment of the gate voltage $V_G$ (to maintain the operating point of the sensor) a continuous heating of the sensor is not needed. Only if the gate voltage $V_G$ leaves a pre-defined target range, the heater may be again activated to refresh the Hall plate, and the measurement cycle starts over. The check, whether the gate voltage $V_G$ is still within the desired target range is labelled as step 123 in the example of FIG. 13.

As an alternative, the refreshing of the gas-sensitive Hall-plate may be time-triggered. In this case, the Hall plate is refreshed when a pre-defined cycle time has elapsed. When using two sensors, these could be operated in an alternating manner so that one sensor is refreshing (heater active) while the other sensor is in measuring mode (see FIG. 13, step 122).

Figure 14A:
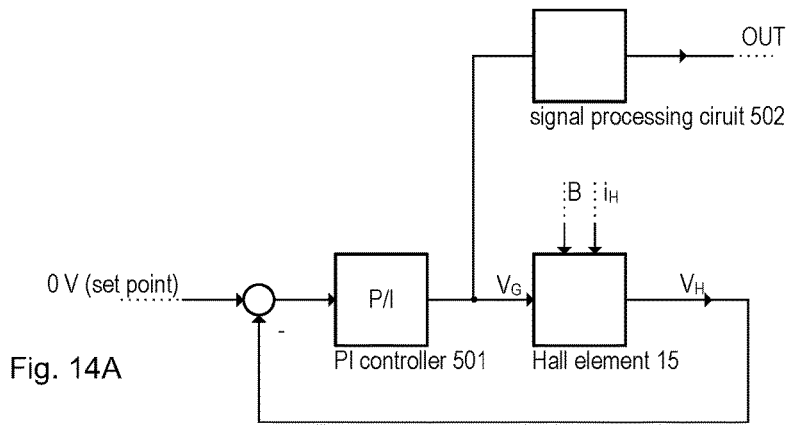
FIGS. 14A-14C illustrates by means of block an timing diagrams two exemplary regulation schemes for regulating the gate voltage applied to the back-gate of a Hall element.

FIG. 14 illustrates by means of block an timing diagrams two exemplary regulation schemes for regulating the gate voltage applied to the back-gate of a Hall element. FIG. 14a illustrates a control loop, which may be used to continuously regulate the gate voltage $V_G$ for a specific Hall element 15 such that the Hall voltage $V_H$ tapped at the Hall element 15 is kept at a level of substantially zero volts. That is, the set-point for the control loop is zero. In this case the Hall element 15 is continuously operated in the most-sensitive operation point, i.e. the zero-crossing of the curve in the bottom diagram of FIG. 8. In this regard, reference is made to FIGS. 8 and 9 the respective description. As the Hall voltage $V_H$ is substantially zero in this example, in information about the concentration of gas atoms/molecules (or information about whether gas atoms/molecules have been detected) is solely in the gate voltage $V_G$ applied to the back gate 10 of the Hall element 15. If the gate voltage $V_G$ exceeds a pre-defined value, a refresh of the Hall element 15 may be triggered, e.g., by activation of the micro-heater. In the present examine a proportional/integral (PI) controller 501 is used to adjust the gate voltage $V_G$ in order to maintain the Hall voltage $V_H$ at zero level. However, other controller types may be used.

Figure 14B:
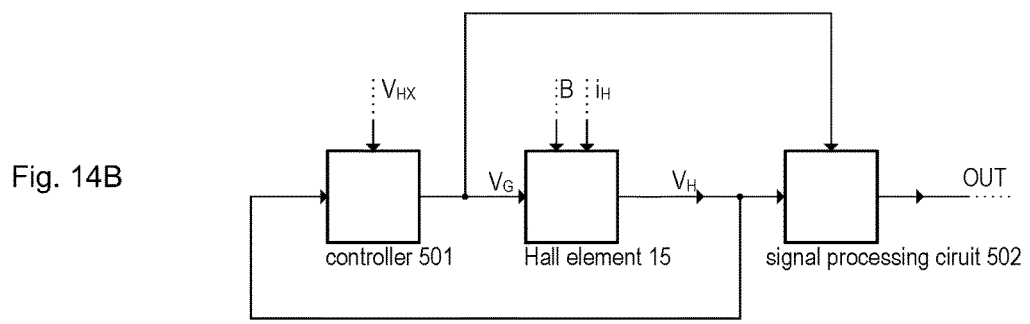
Figure 14C:
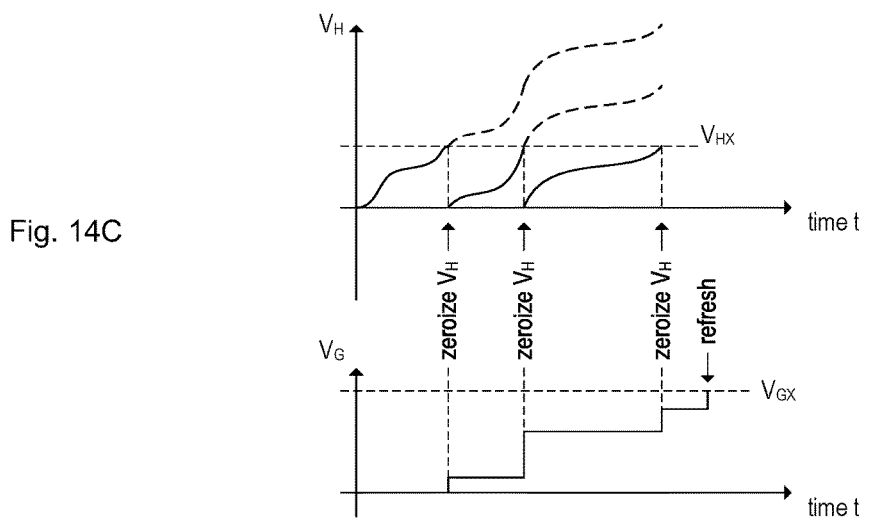

FIG. 14b illustrates another example of a control loop for adjusting the gate voltage $V_G$. Different from the previous example, the Hall voltage $V_H$ is not continuously regulated to zero but rather zeroized either in regular time intervals or when the Hall voltage $V_H$ exceeds a pre-defined threshold level $V_{HX}$. However, more complex schemes for zeroizing the Hall voltage may be used. In the present example, the Hall voltage $V_H$ is zeroized (by appropriate adjustment of the gate voltage $V_G$) each time when the Hall voltage reaches or exceeds the threshold level $V_{HX}$. This function is further illustrated by the timing diagram of FIG. 14c. Each time the Hall voltage $V_H$ reaches the threshold $V_{HX}$, the gate voltage $V_G$ is adjusted to set the Hall voltage $V_H$ to zero. Then the gate voltage is constant until the Hall voltage $V_H$ again reaches the threshold $V_{HX}$. When the gate voltage $V_G$ leaves a predefined range (e.g. from $-V_{GX}$ to $V_{GX}$), the measurement may be paused and the Hall element may be refreshed, e.g. by activation of the micro-heater (see FIGS. 4-6).

While various embodiments of the invention have been described, it will be apparent to those of ordinary skill in the art that many more embodiments and implementations are possible within the scope of the invention. Accordingly, the invention is not to be restricted except in light of the attached claims and their equivalents. With regard to the various functions performed by the components or structures described above (assemblies, devices, circuits, systems, etc.), the terms (including a reference to a "means") used to describe such components are intended to correspond, unless otherwise indicated, to any component or structure that performs the specified function of the described component (i.e., that is functionally equivalent), even if not structurally equivalent to the disclosed structure that performs the function in the exemplary implementations of the invention illustrated herein.

The invention claimed is:

1. A chemically sensitive Hall device comprising:
   a substrate;
   a chemically sensitive layer arranged on the substrate and operably interacting with atoms or molecules of a gaseous or liquid fluid;
   force electrodes connected to the chemically sensitive layer for feeding a sensor current through the chemically sensitive layer along a first direction;
   sense electrodes connected to the chemically sensitive layer to tap a Hall voltage at the chemically sensitive layer along a second direction;
   a back gate arranged on or integrated in the substrate; the back gate being isolated from the chemically sensitive layer by an isolation layer.

2. The chemically sensitive Hall device according to claim 1 further comprising:
   a control circuit coupled to the force electrodes and configured to generate the sensor current, and further coupled to the back-gate and configured to apply a gate voltage to the back-gate for tuning of the Hall voltage.

3. The chemically sensitive Hall device according to claim 2, wherein the control circuit is configured to apply the gate voltage to the back gate such that the Hall voltage is adjusted to zero.

4. The chemically sensitive Hall device according to claim 2, wherein the control circuit further coupled to the sense electrodes and configured to regularly or continuously regulate the gate voltage applied to the back gate such that the Hall voltage is maintained at a level of substantially zero volts.

5. The chemically sensitive Hall device according to claim 1, wherein a coil is integrated in the substrate subjacent to the chemically sensitive layer.

6. The chemically sensitive Hall device according to claim 5, wherein the coil is operably supplied with current to generate a magnetic field having a field component perpendicular to a top surface of the chemically sensitive layer.

7. The chemically sensitive Hall device according to claim 5, wherein the coil is configured to be operated as heating coil to generate heat for the heating of the chemically sensitive layer.

8. The chemically sensitive Hall device according to claim 1, further comprising:
   a permanent magnet configured to generate a magnetic field having a filed component perpendicular to a top surface of the chemically sensitive layer.

9. The chemically sensitive Hall device according to claim 1, further comprising:
   a heating circuit including a heat generating element, which is configured to heat up a gas-sensitive layer to desorb atoms or molecules from the chemically sensitive layer.

10. The chemically sensitive Hall device according to claim 9, wherein the back-gate region is used as heat generating element.

11. The chemically sensitive Hall device according to claim 9, wherein the chemically sensitive layer is used as heat generating element, and the sensor current is increased to heat up the chemically sensitive layer.

12. The chemically sensitive Hall device according to claim 9, wherein the heating circuit is configured to cyclically heat up the gas-sensitive layer.

13. A sensor array including at least two chemically sensitive Hall devices in accordance with claim 1, wherein the at least two chemically sensitive Hall devices are integrated in one substrate or in one sensor package.

14. The chemically sensitive Hall device according to claim 1, wherein the sense electrodes are connected to the chemically sensitive layer directly.

15. The chemically sensitive Hall device according to claim 1, wherein the force electrodes and the sense electrodes are formed in a same layer.

16. A method for operating a sensor which includes a chemically sensitive Hall element arranged on a substrate; the method comprising:
  applying a sensor current to the chemically sensitive Hall element so that the sensor current passes through the Hall element in a first direction,
  sensing a Hall voltage at the Hall element along a second direction substantially perpendicular to the first direction; and
  applying a gate voltage to a back-gate arranged on or integrated in the substrate, the gate voltage being responsive to the Hall voltage.

17. The method according to claim 16 further comprising:
  heating the chemically sensitive Hall element to desorb atoms or molecules from the chemically sensitive Hall element.

18. The method according to claim 17, wherein the heating is performed regularly or periodically for a defined duration.

19. The method according to claim 17, wherein the heating is performed for a defined duration, when the gate voltage leaves a pre-defined target range.

20. The method according to claim 17, wherein the heating is performed for a defined duration, when a pre-defined cycle time has elapsed.

21. The method according to claim 16, wherein the gate voltage is regularly or periodically adjusted such that the Hall voltage becomes zero.

22. A chemically sensitive sensor array comprising:
  at least two Hall elements having a chemically sensitive layer, which operably interacts with atoms or molecules of a gaseous or liquid fluid; each Hall element having force electrodes for feeding a sensor current through the respective Hall element, sense electrodes for tapping a Hall voltage at the respective Hall element, and a back gate, which is arranged subjacent to the chemically sensitive layer, is isolated from the chemically sensitive layer by an isolation layer, and has a gate voltage responsive to the Hall voltage.

23. The chemically sensitive sensor array of claim 22, wherein at least two of the Hall elements have chemically sensitive layers, which are chemically functionalized differently to provide sensitivity to different atoms or molecules.

24. The chemically sensitive sensor array of claim 22, further comprising:
  circuitry configured to select one or more of the Hall elements; the sensor current being fed at least through the selected Hall elements, the back gate voltage being applied to the back gate(s) of at least the selected Hall elements, and the Hall voltage being tapped at least at the selected Hall elements.

25. The chemically sensitive sensor array of claim 24, wherein two or more Hall elements are selected and the selected Hall elements are connected in parallel.

26. The chemically sensitive sensor array of claim 24, wherein the Hall elements are selected sequentially.

27. The chemically sensitive sensor array of claim 24, wherein the circuitry includes at least a multiplexer and a demultiplexer.

* * * * *